(12) United States Patent
Slautterback et al.

(10) Patent No.: US 6,422,242 B1
(45) Date of Patent: Jul. 23, 2002

(54) HERNIA BELT

(75) Inventors: Ernest Gerald Slautterback, Coral Springs; Nicole D. Greene; Rhonda M. Machin, both of Weston, all of FL (US)

(73) Assignee: FLA Orthopedics, Inc., Miramar, FL (US)

( * ) Notice: Subject to any disclaimer, the term of this patent is extended or adjusted under 35 U.S.C. 154(b) by 17 days.

(21) Appl. No.: 09/642,377

(22) Filed: Aug. 21, 2000

(51) Int. Cl.$^7$ ................................................ A61F 13/00
(52) U.S. Cl. ........................ 128/846; 128/96.1; 128/95.1
(58) Field of Search ................................ 128/846–848, 128/95.1, 96.1, 118.1; 121/96.1; 602/5, 13, 19

(56) References Cited

U.S. PATENT DOCUMENTS

| 3,754,549 A | 8/1973 | Nelkin |
| 4,059,103 A | 11/1977 | Glaser |
| 4,351,325 A | 9/1982 | Walker |
| 4,416,272 A | 11/1983 | Nelkin |
| 4,671,264 A | 6/1987 | Frangi |
| 4,787,379 A | 11/1988 | Yeh |

FOREIGN PATENT DOCUMENTS

| GB | 2-268-689 | * | 6/1993 | ...................... 5/24 |

* cited by examiner

*Primary Examiner*—Michael A. Brown
*Assistant Examiner*—Lalita M. Hamilton

(57) ABSTRACT

A hernia belt which is provided in two parts, comprising an abdominal belt portion, having a pair of leg straps which extend downwardly for passing between the legs of a wearer, and a separate back belt portion, which extends around the back of the wearer. Virtually the entire face of the exterior of the abdominal belt portion is formed of hook or loop material, which engages with mating loop/hook surfaces on the ends of the back belt portion. The combination of the abdominal belt portion having virtually its entire surface covered with hook/loop material, and a back belt portion with hook/loop material at its ends, makes it possible to provide virtually universal or "fits all" hernia support.

4 Claims, 6 Drawing Sheets

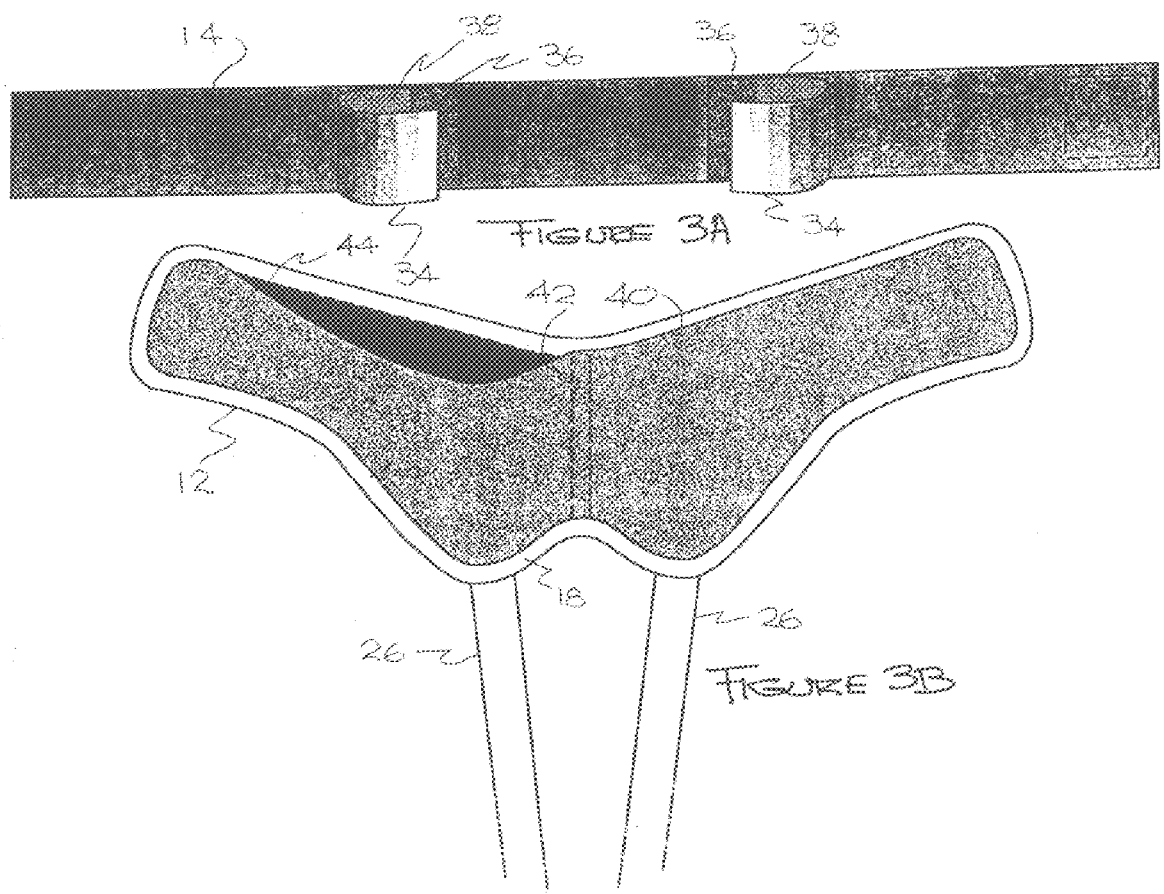

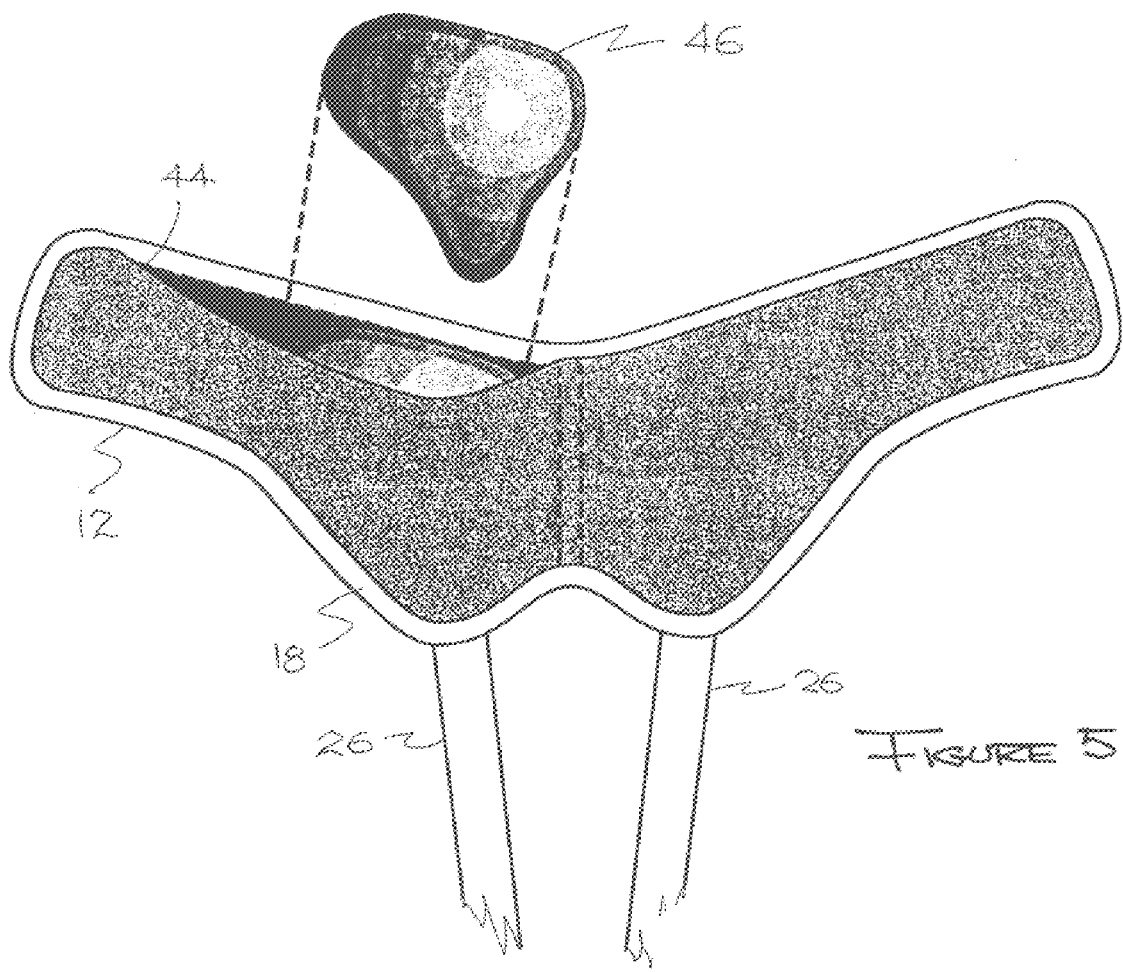

HERNIA BELT

FIELD OF THE INVENTION

The present invention is directed to a hernia belt or truss useful in supporting abdominal hernias.

BACKGROUND OF THE INVENTION

Hernia belts have been well known for many years and have been proposed and used in many different forms. Examples of some of these differing devices are reflected in the patent literature.

U.S. Pat. No. 4,059,103, issued Nov. 22, 1977, to Glaser, describes a one-piece bi-sexual garment. A narrow neck section of the support passes through the crotch of the wearer and anchors the bottom part, while a first belt like elastic band connects and supports the upper parts of the front and rear sections, and is secured to both. A second belt-like elastic band encircles the hips of the wearer below the first elastic band, and is fastened only to the rear portion of the support. The elastic bands extend over the hips to provide up-lift.

U.S. Pat. No. 4,671,264, issued Jun. 9, 1987, to Frangi, describes an underpant brief and hernial truss. An elastic belt is disposed at the circumferential upper edge of the brief, and a pair of at least partly elastic bands has upper ends which are affixed to the elastic belt and pass laterally of the crotch of the pant, adjacent the leg holes of the brief. These bands include an inelastic segment on the front of the underpant extending diagonally across a hernia affectable region of the wearer. Pockets are included over the hernia affectable region for receiving a retaining pad.

U.S. Pat. No. 4,416,272, issued Nov. 22, 1983 to Nelkin, describes another combination of underpant and hernial truss. This patent describes a brief having a front, rear and crotch portions with spaced leg holes. A truss pad is attached to the front portion and protrudes inwardly to the brief to engage and support a herniated abdominal area. An adjustable length belt encircles the brief and is connected to the front portion adjacent the pad for directing hernia retaining force thereon. The belt is free from securement to the rear portions of the brief for selective movement upwardly and downwardly to adjust to the wearer's comfort.

A clean copy of amended page 2 is attached.

U.S. Pat. No. 4,351,325, issued Sep. 28, 1982, describes a wide roll-on belt to which the pressure pad for bearing on the area of the hernia is indirectly attached by an arrangement including a rigid stay member. A strap extends from a lower edge of the pad between the wearer's legs to keep the pad pressed against the body by reaction with the rigid stay, even when movement tends to displace the adjacent part of the belt away therefrom, as when sitting or stooping.

U.S. Pat. No. 4,787,379, issued Nov. 29, 1988, to Yeh, describes a hernia truss comprising a belt which encloses a flexible and bendable spring metal band. Attached to one end of this belt is a soft pad supported upon a round metal plate. The pad is intended to overlie the hernial region when the ends of the belt are fastened together.

U.S. Pat. No. 3,754,549, issued Aug. 28, 1973, to Nelkin, describes an essentially one piece truss belt which is adapted for adjustment in circumference. The adjustment entails the belt being open at the back and having a rather complex fold and strap arrangement for determining the belt circumference.

While the foregoing prior devices purport to serve their intended purposes, for the most part, their designs are such as to produce a significant degree of complexity of adjustment and/and or uncomfortableness for the wearer.

SUMMARY OF THE INVENTION

The invention relates to a hernia belt which is provided in two basic parts which together provide a maximum of adjustability, adaptability, and comfortableness. The two piece hernia belt comprises a soft abdominal belt portion, which is adapted to extend around the abdomen and carry one or two removable hernia pads. Attached to this abdominal portion of the belt are a pair of spaced leg straps which extend downwardly for passing between the legs of a wearer. The abdominal portion of the belt is held in place on a wearer by adjustable attachment to a separate back belt portion, which extends around the back of the wearer.

According to the invention, virtually the entire face of the exterior of the abdominal belt portion is formed of hook or loop material, preferably loop material. This hook/loop surface engages with mating loop/hook surfaces on the ends of the back belt portion. By this combination of an abdominal belt portion having virtually its entire surface covered with hook/loop material, and a sufficiently long back belt portion with hook/loop material at its ends, it is possible to provide virtually universal or "fits all" hernia support.

At the same time, the leg straps which depend from the abdominal portion of the belt are adapted to be adjustably secured to the back belt portion through hook/loop attachment. This adjustable leg strap arrangement interacts with the adjustable waist size in providing the virtually universal size hernia belt. The abdominal belt portion carries one or more pockets for receiving one or more pads (right or left, or right and left), adapted to provide the desired hernial support.

It is a primary of object of the present invention to provide an improved hernia belt, which eliminates or alleviates the shortcomings of the foregoing exemplar hernia belts described in the patent literature.

It is another object of the invention to provide such an improved hernia belt which provides easy adjustment, is comfortable to the wearer, and which provides a fit for virtually all waist sizes.

DESCRIPTION OF THE DRAWINGS

Further objects and advantages of the present invention will become apparent as the following description of illustrative embodiments proceeds, taken in conjunction with the accompanying drawings in which:

FIG. 2A shows a front elevation view of the interior of the back belt portion with its hook faced securing members at its ends. FIG. 2B shows a front perspective view of the abdominal portion of the belt showing its fully loop material surfaced face panel.

FIGS. 3A and 3B also show the hernia belt in a disassembled condition. FIG. 3A shows a back elevation view of the exterior of the back belt portion showing its spaced and folded leg strap securing flaps. FIG. 3B shows the soft fabric interior face of the abdominal belt portion and its pockets for receiving one or two hernia pads, with the left pocket being shown with its top opened to receive a pad.

FIG. 5 is similar to FIG. 3B and shows a hernia pad before and after being inserted in the left pocket of the abdominal portion of the hernia belt.

DETAILED DESCRIPTION

Figure 1:
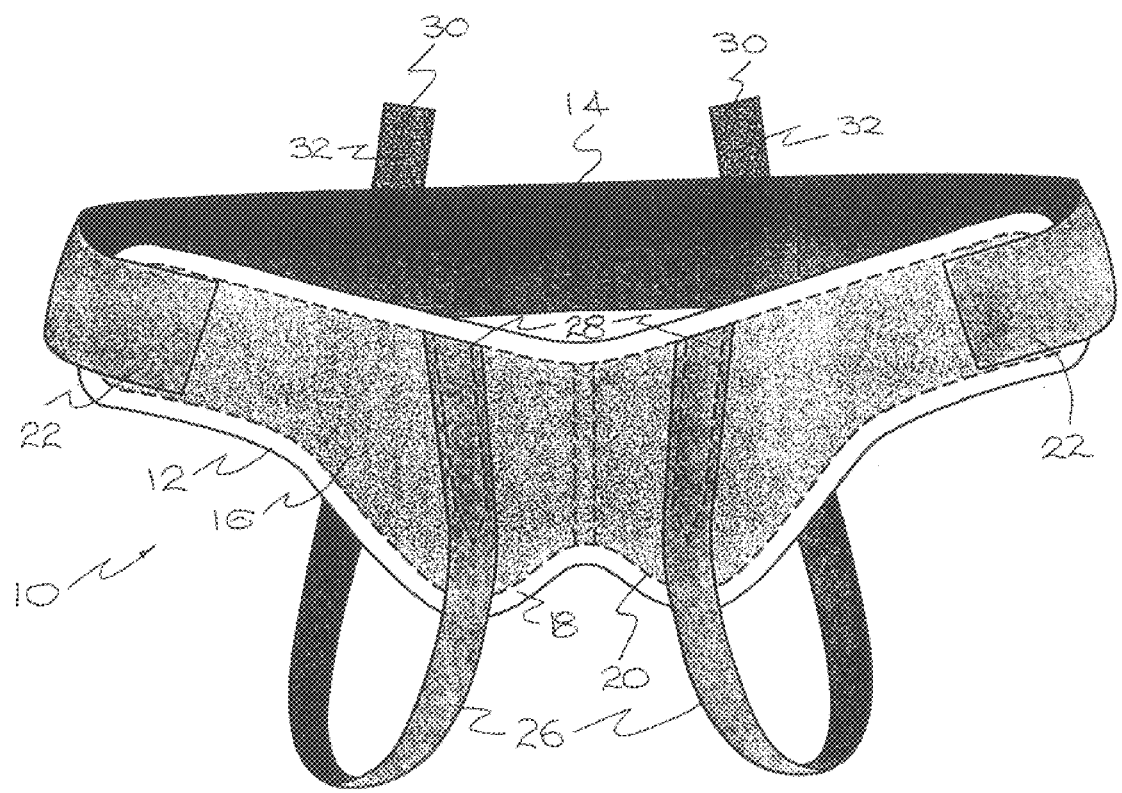
FIG. 1 is a perspective front view of the hernia belt with the ends of the back belt portion releasably secured to the face panel of the abdominal belt portion.

Referring to FIG. 1, a hernia belt according to a preferred embodiment of the invention is shown generally at 10 in an assembled condition. The belt is formed in two pieces comprising an abdominal portion 12, which is secured to a back belt portion 14 to fit around the waist of a wearer. According to the invention the face of the abdominal belt portion 12 is covered with soft loop type hook/loop material indicated at 16. The edges of the abdominal belt portion preferably are covered with a soft fabric edging 18 sewn to the abdominal belt portion in a line of stitching represented by the broken line 20. It will be apparent that other means of securement of the edging may also be used. While it is preferred that the face of the abdominal belt portion be covered with loop material, it is also within the comprehension of the invention to substitute hook material.

Figure 2A:
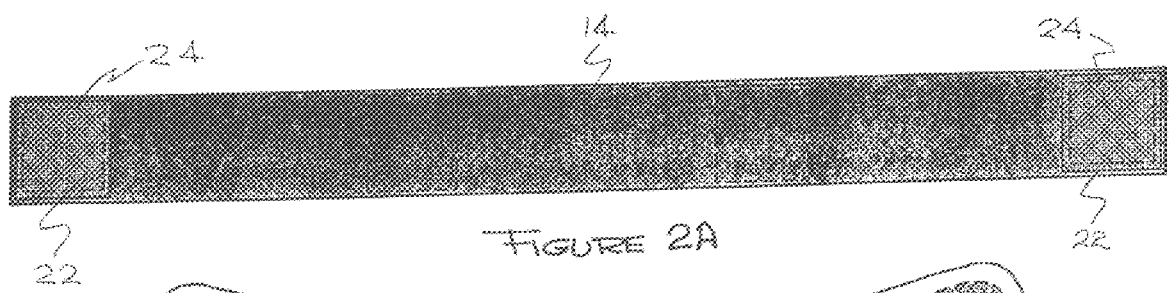
FIGS. 2A and 2B show the hernia belt in a disassembled condition.

The back belt portion 14 is preferably inelastic, and is provided with hook material pads 22 on the inner surfaces of its ends. These are best seen in FIG. 2A and may be sewn or otherwise secured to the back belt portion. An illustrative line of stitching is shown by the broken lines 24. These hook material pads provide adjustable attachment of the back belt portion 14 to the loop material face of the abdominal belt portion 12. While this embodiment of the invention has been described as having the outward surface of the abdominal belt portion preferably surfaced with loop material, it will be obvious to those skilled in the art that the positions of the loop and hook materials on the abdominal belt portion and on the ends of the back belt portion could be reversed, if desired.

It is a feature of the invention that this provision of an abdominal belt portion with its face substantially fully covered with hook/loop material, when coupled with the use of a back belt portion having mating hook/loop material at its ends, provides of very high range of adjustment of waist sizes to a single hernia belt. The back belt portion is preferably of a length which will substantially completely encircle the waist of the smallest anticipated wearer. With such a back belt portion and an adominal belt portion having hook/loop material over its entire outer face, the ends of the back belt portion may be attached to the abdominal belt portion at positions extending from its extreme end edges all the way to the center thereof. This arrangement permits a single sized hernia belt to fit virtually all anticipated wearers.

A pair of leg straps 26 depend from the front surface of the abdominal belt portion for passing between the legs of a wearer. These leg straps may be fastened to the face of the abdominal belt portion in any suitable manner, such as by stitching 28. The ends 30 of the leg straps are then adjustably secured to the rear of the back belt portion, as presently will be described in further detail. The leg straps are sewn to the abdominal belt portion in a slightly converging relationship to one another, as may be seen in FIGS. 1 and 2B.

Figure 2B:
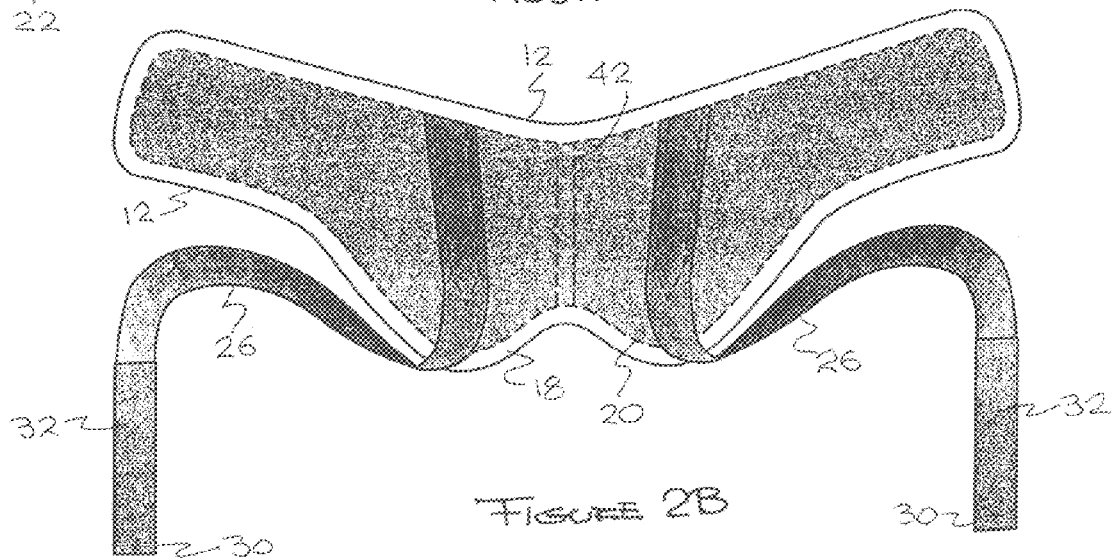

FIG. 2A shows the inside of the back belt portion 14 with its hook/loop pads 22 at the ends thereof. FIG. 2B shows the outside of the abdominal belt portion 12 with its attached leg straps 26. The ends 30 of the leg straps 24 are provided with a surfacing of loop material 32 over an extended portion of both sides or surfaces thereof. The function of this material is presently described.

Referring to FIG. 3A, the outer surface of the back portion of the hernia belt is shown. A pair of spaced securing flaps 34 are attached to the outer surface of the back belt portion in any suitable manner, such as by sewing of the secured ends of the flaps to the back belt portion. Alternatively, these flaps may be secured to the back belt portion by hook and loop attachment of one end thereof.

As seen in FIG. 3A, the flaps 34 are adapted to be reversely folded back upon themselves to form loops. The flaps are provided with pads 36 of loop material at the ends thereof, which are secured to the back belt portion, as by the sewing of the flap ends to the back belt portion. The remainder of the interior surfaces of the flaps are formed of hook material 38. In this manner the flaps 34 may be fastened to themselves in a releasable closed loop configuration by locking the hook surfaced free ends to the loop pads at the sewn ends.

Figure 6:
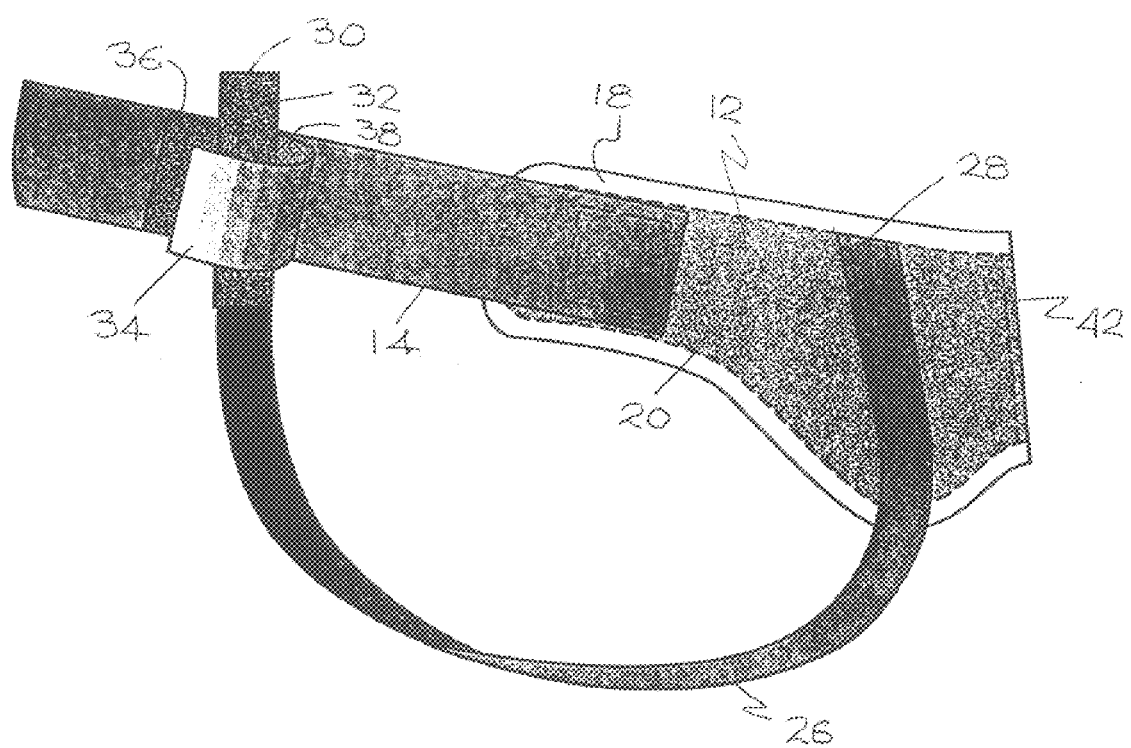
FIG. 6 is a right side view of one half of an assembled hernia belt, and shows the exterior of the right half of the abdominal portion of the hernia belt and of the right half of the back portion of the belt, which is releasably secured thereto.

As has been previously described, and as shown in FIGS. 2B and 6, the ends 30 of the leg straps 26 are covered on both sides with loop fastening material, as shown at 32. In fastening the leg straps, the flaps 34 are initially preferably open. The loop covered ends 30 of the leg straps 26, which are now in the back of the wearer, are pulled upwardly by the wearer, to secure a comfortable fit between the legs of the wearer.

The loop material 32 on the sides of the leg strap end surfaces 30 which face the body of the wearer, are then pressed inwardly toward the body of the wearer and toward the outside of the back belt. This loop material is pressed into mating engagement with the outwardly facing portions of the hook material 38 on the inner surfaces of the flaps 34 adjacent their sewn loop ends. The flaps are then folded into their loop configuration and the free ends of the flaps 34 are pressed inwardly. This forces the hook material on the inner surfaces of the looped flaps to engage the loop material on both sides of the surfaces of the ends of the leg straps. In this manner a very secure yet adjustable releasable fastening is formed, as may be seen in FIG. 6.

The free ends of the flaps 34 are then further pressed inwardly toward the body of the wearer so as to engage the hook material on the inside surfaces of the free ends of the flaps with the loop material pads 36, which are sewn to the back belt portion. While this securement of the ends of the leg straps to the back belt portion of the hernia belt is preferred, it will be obvious to those skilled in the art that other hook/loop securement could also be used.

FIG. 3B shows the preferably soft fabric interior layer 40 of the abdominal belt portion 12. This interior layer 40 is attached to the outer face layer 16 of the abdominal belt portion by the stitching 20 securing the edging 18, as seen in FIGS. 1 and 2B. In addition, the layers of the abdominal belt portion are secured together in vertical lines of center stitching shown by broken lines at 42.

Referring to FIGS. 3B and 5, the upper edge 44 of at least one side of the interior face layer 40 of the abdominal belt portion 12 is left free and is not fastened within the edging. This construction forms one or two pockets in the abdominal belt portion for receiving one or two hernia pads. The left pocket in FIG. 3B is shown with its top opened to receive such a pad.

Figures 4A, 4B:
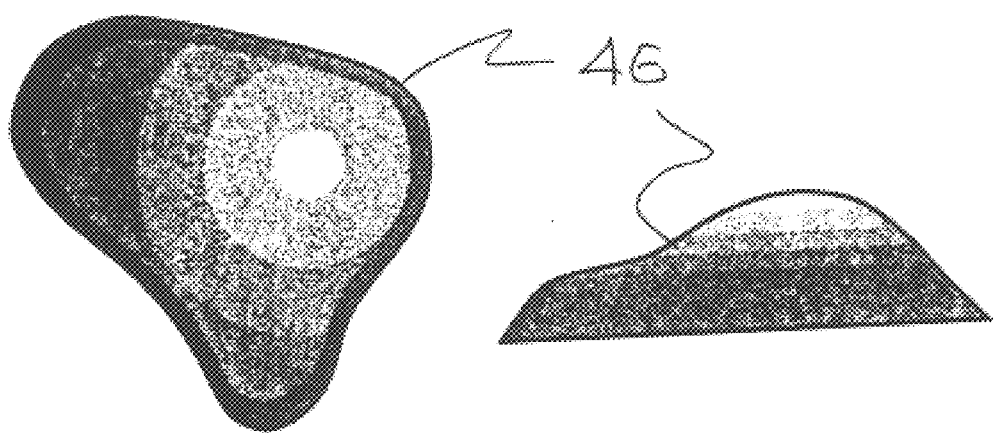
FIGS. 4A and 4B show respectively a top plan view and a side elevation view of a hernia pad.

Referring to FIG. 5, a hernia pad 46 is shown in the process of being inserted into a pocket. The uppermost representation of the hernia pad 46 in that figure shows it in its pre-insertion position. The lowermost representation of the hernia pad in FIG. 5 shows it in an inserted position. The hernia pad itself may be of a generally kidney shape and is shown in plan and side views in FIGS. 4A and 4B, respectively.

It will be readily seen by one of ordinary skill in the art that the present invention fulfills the objects and objectives set forth above. After reading the foregoing specification, one of ordinary skill will be able to effect various changes, substitutions of equivalents and to vary other aspects of the invention as broadly disclosed herein. It is therefore intended that the protection granted hereon be limited only by the definition contained in the appended claims and equivalents thereof.

What is claimed is:

1. A hernia belt comprising:

an abdominal belt portion and a separate elongated back belt portion, said abdominal belt portion having outer and inner layers secured together at least in a major portion of their lower edges, said layers having upper edges which are free of one another over at least portions of their upper edges for a distance sufficient to form at least one pocket for receiving a hernia pad, the outer of said layers being formed of a releasable hook/loop fastening material, and the inner of said layers being formed of a soft material, said elongated back belt portion having at its ends pads of releasable hook/loop fastening material for mating with the hook/loop material on said abdominal belt portion to releasably and adjustably fasten said belt portions together around the abdomen and waist of a wearer, said releasable hook/loop fastening material on said abdominal belt portion substantially fully covering the exterior surface of said abdominal belt portion so as to provide a wide range of adjustment and waist sizes, and spaced leg straps attached to said abdominal belt portion and extending downward, said leg straps having hook/loop material extending along at least one surface of their end portions for adjustable and releasable attachment to spaced areas on the outer surface of said separate elongated back belt portion.

2. A hernia belt according to claim 1 wherein said outer and inner layers of said abdominal belt portion are substantially co-terminous, and said leg straps are fastened to the outer layer material to provide support to hold at least one pad in desired support position relative to the wearer, said leg straps through their adjustable attachability to the outer surface of said back belt portion providing hernia belt size and support adaptability subject to adjustment by the wearer, the ends of said back belt portion being securable to the outer surface of said abdominal belt portion over a range of positions extending from substantially the mid-section of said abdominal belt portion to the distal ends thereof.

3. A hernia belt according to claim 2 wherein said back belt portion is of a length to substantially encircle the waist of the smallest anticipated wearer.

4. A hernia belt according to claim 3 wherein said hook/loop material of said outer layer of said abdominal belt portion comprises loop material.

* * * * *